US007358407B2

(12) United States Patent
Parks et al.

(10) Patent No.: US 7,358,407 B2
(45) Date of Patent: *Apr. 15, 2008

(54) BROMINATION PROCESS

(75) Inventors: John C. Parks, Baton Rouge, LA (US); David H. Knoebel, Homer, LA (US); Lawrence M. Jenkins, Magnolia, AR (US); George H. Ransford, Magnolia, AR (US); Gary L. Bowman, Jr., Stamps, AR (US); Saadat Hussain, Baton Rouge, LA (US)

(73) Assignee: Albemarle Corporation, Richmond, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/550,287

(22) Filed: Oct. 17, 2006

(65) Prior Publication Data

US 2007/0088184 A1    Apr. 19, 2007

Related U.S. Application Data

(63) Continuation of application No. 11/157,104, filed on Jun. 20, 2005, now Pat. No. 7,179,950, which is a continuation of application No. 10/845,801, filed on May 14, 2004, now Pat. No. 6,974,887, which is a continuation of application No. 10/445,554, filed on May 27, 2003, now Pat. No. 6,768,033, which is a continuation of application No. 10/225,951, filed on Aug. 21, 2002, now Pat. No. 6,603,049, which is a continuation of application No. 08/658,983, filed on Jun. 4, 1996, now Pat. No. 6,518,468, which is a continuation of application No. 08/338,711, filed on Nov. 14, 1994, now abandoned, which is a continuation-in-part of application No. 08/317,792, filed on Sep. 16, 1994, now abandoned, which is a continuation of application No. 09/888,246, filed on Jun. 22, 2001, now Pat. No. 6,958,423, which is a continuation of application No. 08/658,983, filed on Jun. 4, 1996, now Pat. No. 6,518,468.

(51) Int. Cl.
*C07C 25/18* (2006.01)
*C07C 22/04* (2006.01)

(52) U.S. Cl. ........................ 570/190; 570/206; 570/208
(58) Field of Classification Search ................ 570/190, 570/206, 208
See application file for complete search history.

(56) References Cited

U.S. PATENT DOCUMENTS

| 2,022,634 | A | 11/1935 | Britton et al. |
| 2,033,612 | A | 3/1936 | Clark et al. |
| 2,240,718 | A | 5/1941 | Schiffman et al. |
| 2,244,284 | A | 6/1941 | Britton et al. |
| 2,556,721 | A | 6/1951 | Gislon et al. |
| 2,607,802 | A | 8/1952 | Britton et al. |
| 2,979,637 | A | 4/1961 | Welna |
| 3,029,295 | A | 4/1962 | Thermet et al. |
| 3,062,899 | A | 11/1962 | Sax |
| 3,141,860 | A | 7/1964 | Sauer et al. |
| 3,232,959 | A | 2/1966 | Hahn |
| 3,285,965 | A | 11/1966 | Jenkner |
| 3,331,797 | A | 7/1967 | Kopetz et al. |
| 3,366,694 | A | 1/1968 | Thompson |
| 3,441,524 | A | 4/1969 | Burger et al. |
| 3,591,645 | A | 7/1971 | Selwitz |
| 3,639,302 | A | 2/1972 | Brown et al. |
| 3,711,562 | A | 1/1973 | Maul et al. |
| 3,733,368 | A | 5/1973 | Burk |
| 3,752,856 | A | 8/1973 | Nagy et al. |
| 3,763,248 | A | 10/1973 | Mitchell |
| 3,833,674 | A | 9/1974 | Brackenridge |
| 3,839,140 | A | 10/1974 | Tyler et al. |
| 3,845,146 | A | 10/1974 | Moore et al. |
| 3,850,882 | A | 11/1974 | Underwood et al. |
| 3,883,481 | A | 5/1975 | Kopetz et al. |
| 3,911,033 | A | 10/1975 | Schaffner et al. |
| 3,931,081 | A | 1/1976 | Dany et al. |
| 3,959,387 | A | 5/1976 | Brackenridge |
| 3,962,164 | A | 6/1976 | Praetzel et al. |
| 3,965,197 | A | 6/1976 | Stepniczka |
| 3,969,387 | A | 7/1976 | Merkl |
| 3,971,758 | A | 7/1976 | Anderson et al. |
| 4,024,092 | A | 5/1977 | Sonnenberg |
| 4,067,930 | A | 1/1978 | Versnel et al. |
| 4,072,658 | A | 2/1978 | Okamoto et al. |
| 4,130,605 | A | 12/1978 | Barkhuff, Jr. |
| 4,150,066 | A | 4/1979 | Kudo et al. |
| 4,223,169 | A | 9/1980 | Barda |
| 4,230,821 | A | 10/1980 | Bertrand |
| 4,276,189 | A | 6/1981 | Jackisch |
| 4,287,373 | A | 9/1981 | Garman et al. |
| RE30,778 | E | 10/1981 | Hahn et al. |

(Continued)

FOREIGN PATENT DOCUMENTS

CA         708209        4/1965

(Continued)

OTHER PUBLICATIONS

Green, et al.; "Flame Retarding Thermoplastic Styrenic Resins"; Fire Retardants: Proceedings of 1974 International Symposium on Flammability And Fire Retardants; Cornwall, Ontario Canada; May 1974; Technomic Publishing Co. Inc.; pp. 68-76.

(Continued)

*Primary Examiner*—Barbara P. Badio

(57) ABSTRACT

This invention relates to a novel process which comprises feeding a mixture formed from diphenylethane and bromine to a stirrable reaction mass comprised of bromine and a bromination catalyst to yield a decabromodiphenylethane wet cake which can be most economically treated to provide a high quality decabromodiphenylethane product.

20 Claims, 1 Drawing Sheet

U.S. PATENT DOCUMENTS

| | | | |
|---|---|---|---|
| 4,301,058 A | 11/1981 | Neukirchen et al. | |
| 4,327,227 A | 4/1982 | Ayres et al. | |
| 4,348,306 A | 9/1982 | Mischutin | |
| 4,396,730 A | 8/1983 | Imahashi | |
| 4,442,017 A | 4/1984 | Blumberg et al. | |
| 4,505,850 A | 3/1985 | Pearson | |
| 4,521,633 A | 6/1985 | Pedjac | |
| 4,532,287 A | 7/1985 | Bill et al. | |
| 4,569,596 A | 2/1986 | Romanchik et al. | |
| 4,639,481 A | 1/1987 | Giles, Jr. | |
| 4,639,486 A | 1/1987 | Liu | |
| 4,659,021 A | 4/1987 | Bark et al. | |
| 4,666,947 A | 5/1987 | Brichta et al. | |
| 4,717,776 A | 1/1988 | Brackenridge et al. | |
| RE32,606 E | 2/1988 | Stepniczka | |
| 4,740,629 A | 4/1988 | Brackenridge et al. | |
| 4,741,864 A | 5/1988 | Avakian et al. | |
| 4,751,260 A | 6/1988 | Kress et al. | |
| 4,778,933 A | 10/1988 | McKinnie et al. | |
| 4,814,525 A | 3/1989 | Rule et al. | |
| 4,849,547 A | 7/1989 | Stollar et al. | |
| 4,865,880 A | 9/1989 | Silbermann et al. | |
| 4,871,882 A | 10/1989 | Stollar et al. | |
| 4,925,994 A | 5/1990 | Mais et al. | |
| 4,983,781 A | 1/1991 | Desmurs et al. | |
| 4,990,707 A | 2/1991 | Mais et al. | |
| 5,003,117 A | 3/1991 | Hussain | |
| 5,008,477 A | 4/1991 | Hussain | |
| 5,030,778 A | 7/1991 | Ransford | |
| 5,036,126 A | 7/1991 | Rinehart et al. | |
| 5,039,729 A | 8/1991 | Brackenridge et al. | |
| 5,041,687 A | 8/1991 | McKinnie et al. | |
| 5,053,447 A | 10/1991 | Hussain | |
| 5,055,235 A | 10/1991 | Brackenridge et al. | |
| 5,059,650 A | 10/1991 | Goettsch et al. | |
| 5,077,334 A | 12/1991 | Hussain | |
| 5,124,496 A | 6/1992 | Templeton et al. | |
| 5,136,107 A | 8/1992 | Stephens et al. | |
| 5,218,017 A | 6/1993 | Doucet et al. | |
| 5,302,768 A | 4/1994 | Hussain | |
| 5,324,874 A | 6/1994 | Ransford et al. | |
| 5,401,890 A | 3/1995 | Parks | |
| 5,457,248 A | 10/1995 | Mack et al. | |
| 6,518,468 B1 * | 2/2003 | Parks et al. | 570/190 |
| 6,603,049 B1 * | 8/2003 | Parks et al. | 570/190 |
| 6,768,033 B2 * | 7/2004 | Parks et al. | 570/190 |
| 6,958,423 B2 * | 10/2005 | Parks et al. | 570/184 |
| 6,974,887 B2 * | 12/2005 | Parks et al. | 570/190 |
| 7,129,384 B2 * | 10/2006 | Parks et al. | 570/184 |
| 7,179,950 B2 * | 2/2007 | Parks et al. | 570/190 |
| 2005/0234271 A1 | 10/2005 | Parks et al. | |

FOREIGN PATENT DOCUMENTS

| | | |
|---|---|---|
| DE | 87752 | 1/1895 |
| DE | 2027762 | 12/1971 |
| DE | 2148276 | 4/1972 |
| DE | 2400455 | 2/1975 |
| DE | 2521926 | 4/1976 |
| DE | 2950877 A1 | 6/1981 |
| DE | 3422673 A1 | 12/1985 |
| EP | 0265150 A1 | 4/1988 |
| EP | 0347116 A2 | 12/1989 |
| EP | 0447152 A1 | 9/1991 |
| EP | 0469569 A2 | 2/1992 |
| GB | 981833 | 1/1965 |
| GB | 991067 | 5/1965 |
| GB | 1350826 | 4/1974 |
| GB | 1411524 | 10/1975 |
| GB | 1472383 | 5/1977 |
| GB | 1572659 | 7/1980 |
| GB | 2081253 A | 2/1982 |
| JP | 52039639 | 3/1977 |
| JP | 53112822 | 10/1978 |
| JP | 53116332 | 10/1978 |
| JP | 53116333 | 10/1978 |
| JP | 53116334 | 10/1978 |
| JP | 54044623 | 4/1979 |
| JP | 56070059 A | 6/1981 |
| JP | 56070060 | 6/1981 |
| JP | 57045114 | 3/1982 |
| JP | 5173548 | 5/1984 |
| JP | 60166333 | 8/1985 |
| JP | 1095143 A | 4/1989 |
| JP | 1146926 A | 6/1989 |
| JP | 3232825 | 10/1991 |
| WO | WO 9608457 A1 | 3/1996 |
| WO | WO 9615087 A1 | 5/1996 |

OTHER PUBLICATIONS

Gassman, et al.; "The 3-(Fluoromethyl)phenyl Group. A Useful Moiety for the Study of Solvolysis Reactions with Large Negative ρ Values"; The Journal of Organic Chemistry, vol. 47, No. 20; Sep. 1982; pp. 4002-4004.

Inaba et al.; "Highly Reactive Metallic Nickel: Reductive Homocoupling Reagent for Benzylic Mono- and Polyhalides"; The Journal of Organic Chemistry; vol. 49; No. 12; Jun. 1984; pp. 2093-2098.

Corey, et al.; "Silacarbocycles From Ring Expansion"; Journal of Organometallic Chemistry; vol. 210; No. 2; May 1981; pp. 149-161.

Golounin; "Formation of Hexabromobenzene in The Bromination of $(C_6H_5)_2X$ Compounds"; translated from Zhurnal Organicheskoi Khimii; vol. 12; No. 8; pp. 1834-1835; Aug. 1976; Original article submitted Nov. 1975.(2 pages).

Encyclopedia of Polymer Science And Technology; vol. 7; "Fire Retardancy"; 1967; pp. 3.

Kirk-Othmer Encyclopedia of Chemical Technology; John Wiley & Sons, New York; Third Edition; vol. 10; "Halogenated Flame Retardants" 1980; pp. 373.

Kirk-Othmer Encyclopedia of Chemical Technology; John Wiley & Sons, Third Edition; vol. 23; "UV Stabilizers"; 1983; pp. 615-627.

An American National Standard; ASTM Designation: E 308—85—"Standard Method for Computing the Colors of Objects by Using the CIE System"; 1985; pp. 242-289.

An American National Standard; ASTM Designation: D 1925—70—(Reapproved 1988); "Standard Test Method for Yellowness Index of Plastics"; pp. 163-165.

Kerscher, Dr. Utto; "Bromine-Containing Flameproofing Agents For Fireproofing of Plastics"; translated from Kunststoff Journal 13(1), 6, 8,10,14,16; 1979; pp. 1-14.

Kolesnikov, G.S. et al.; "Condensation of Benzene With 1,2-dichloroethane"; Chemical Abstracts; vol. 46; 7084 g; 1952; 1 page.

Butin, K.P. et al.; "Synthesis and Some Properties of Pentachloro and Pentabromobenzyl Compounds of Mercury"; Chemical Abstracts; vol. 98; 98:160866p; 1983; 1 page.

Vogel, Dr. Hans, "Flammfestmachen von Kunstatoffen", Technologie Der Makromolekularen Chemis, p. 49 (not translated), with a 3 page translation of p. 49.

CAS Registry Handbook, 632RL; 84852-53-9; Supplement Part 1; 1983; 1 page.

U.S. Appl. No. 06/758,967, filed Jul. 25, 1985, entitled "polybrominated Diphenylethane Fire Retardant", Mossaad, Amgad S., et al.

* cited by examiner

BROMINATION PROCESS

REFERENCE TO RELATED APPLICATIONS

This application is a continuation of commonly-owned application Ser. No. 11/157,104, filed Jun. 20, 2005, now U.S. Pat. No. 7,179,950 B2, issued Feb. 20, 2007, which is a continuation of commonly-owned application Ser. No. 10/845,801, filed May 14, 2004, now U.S. Pat. No. 6,974,887 B2, issued Dec. 13, 2005, which is a continuation of commonly-owned application Ser. No. 10/445,554, filed May 27, 2003, now U.S. Pat. No. 6,768,033 B2, issued Jul. 27, 2004, which is a continuation of commonly-owned application Ser. No. 10/225,951, filed Aug. 21, 2002, now U.S. Pat. No. 6,603,049 B1, issued Aug. 5, 2003 (the disclosure of which is incorporated herein by reference), which is a continuation of commonly-owned application Ser. No. 08/658,983, filed Jun. 4, 1996, now U.S. Pat. No. 6,518,468 B1, issued Feb. 11, 2003, which is a continuation of commonly-owned application Ser. No. 08/338,711, filed Nov. 14, 1994, now abandoned, which in turn is a continuation-in-part of commonly-owned application Ser. No. 08/317,792, filed Sep. 16, 1994, now abandoned. Application Ser. No. 11/157,104, filed Jun. 20, 2005, is also a continuation of commonly-owned application Ser. No. 09/888,246, filed Jun. 22, 2001, now U.S. Pat. No. 6,958,423 B2, issued Oct. 25, 2005, which in turn is a continuation of the aforesaid application Ser. No. 08/658,983, now U.S. Pat. No. 6,518,468.

BACKGROUND OF THE INVENTION

This invention relates to an improved process for the bromination of diphenylalkanes.

Brominated diphenylalkanes, e.g., decabromodiphenylethane, are known flame retardants for use in polystyrene and polyolefin-based thermoplastic formulations. It is predicted that decabromodiphenylethane will soon become one of the major flame retardants used by the thermoplastic industry. In response to this market opportunity, several decabromodiphenylethane processes have been proposed. See U.S. Pat. Nos. 5,077,334, 5,008,477 and 5,030,778.

While these processes are quite efficacious, there is always a desire to develop more economical and technologically beneficent processes. It is an object of this invention to provide such a process.

THE INVENTION

This invention provides a unique process for producing an intermediate decabromodiphenylethane slurry from which a decabromodiphenylethane wet cake can be more efficiently obtained. Even further, the obtained wet cake is most easily convertible to a high-quality ready-to-use flame-retardant product. The wet cake is characterized by having a lower occluded bromine content than that which is obtainable by prior processes.

The process of this invention comprises: mixing bromine and diphenylethane, the molar ratio of bromine to diphenylethane being greater than about 5:1, but preferably less than about 30:1; and quickly feeding the resultant mix to a stirrable reaction mass comprising bromine and a bromination catalyst to yield decabromodiphenylethane.

It is theorized, though this invention is not to be limited to a particular theory, that the feeding of the bromine/diphenylethane derived mixture (which mixture is very dilute in diphenylethane and/or underbrominated diphenylethane) to the reaction mass favorably affects the crystallization of the decabromodiphenylethane product in the reaction mass so that there is a reduction in the formation of extremely small particles (fines) and so that there is an attenuation of the occluded free bromine content in the crystalline structure. It is believed that by having the bromine present in diluent quantities, as the derived mixture is fed, there is obtained, in the area of the feed, (1) a minimization of the variability of the brominated diphenylethane concentration, and (2) the unlikelihood that the crystallization medium, i.e., the reaction mass, will become excessively supersaturated with decabromodiphenylethane. Thus, good, slowed crystal growth is promoted and crystal nucleation is abated.

In addition, the diluent function of the fed bromine benefits product color. It is theorized that when the derived mixture is fed to the reaction mass there is a transient feed plume formed in the reaction mass. There, the diluent bromine acts as a mass transfer impediment to impede the bromination catalyst contained in the reaction mass from reaching some of the yet to be brominated or underbrominated diphenylethane located in the plume. This is beneficial since it is believed that the bromination catalyst will attack, i.e., cleave, the diphenylethane-C—C-bridge if there is insufficient or no bromination of the diphenylethane prior to contact with the catalyst. The cleaved materials are, in many instances, undesirable color bodies. By impeding the mass transfer of the catalyst, for even a very short period of time, more diphenylethane will have sufficient time to obtain the degree of bromination needed to deter cleavage. Once the plume is dissipated in the reaction mass, and this occurs quickly, the bromination catalyst can then effectively catalyze the reaction to obtain the desired ar-brominated decabromodiphenylethane product.

In addition to diminishing-C—C-cleavage, the dilution effect favorably affects the formation of color bodies by reducing the concentration of bromination loci per unit volume. Since the bromination loci are exothermic, the reduction in their concentration enables the avoidance of obtaining color body producing degradation temperatures at each individual locus. The large amount of bromine around each reaction locus acts as heat sink so that the heat is effectively dissipated.

Generally speaking, the processes of this invention will be most useful to the commercial decabromodiphenylethane producer who deals with large reaction volumes, say larger than about 1,000 L (250 gal). Most commercial reactions will be sized from this minimum up to about 32,000 L (8,000 gal). It is in dealing with large reaction masses where the problems associated with decabromodiphenylethane production are most easily seen as mass transfer and crystallization quality are more problematic.

DETAILED DESCRIPTION

Figure 1:
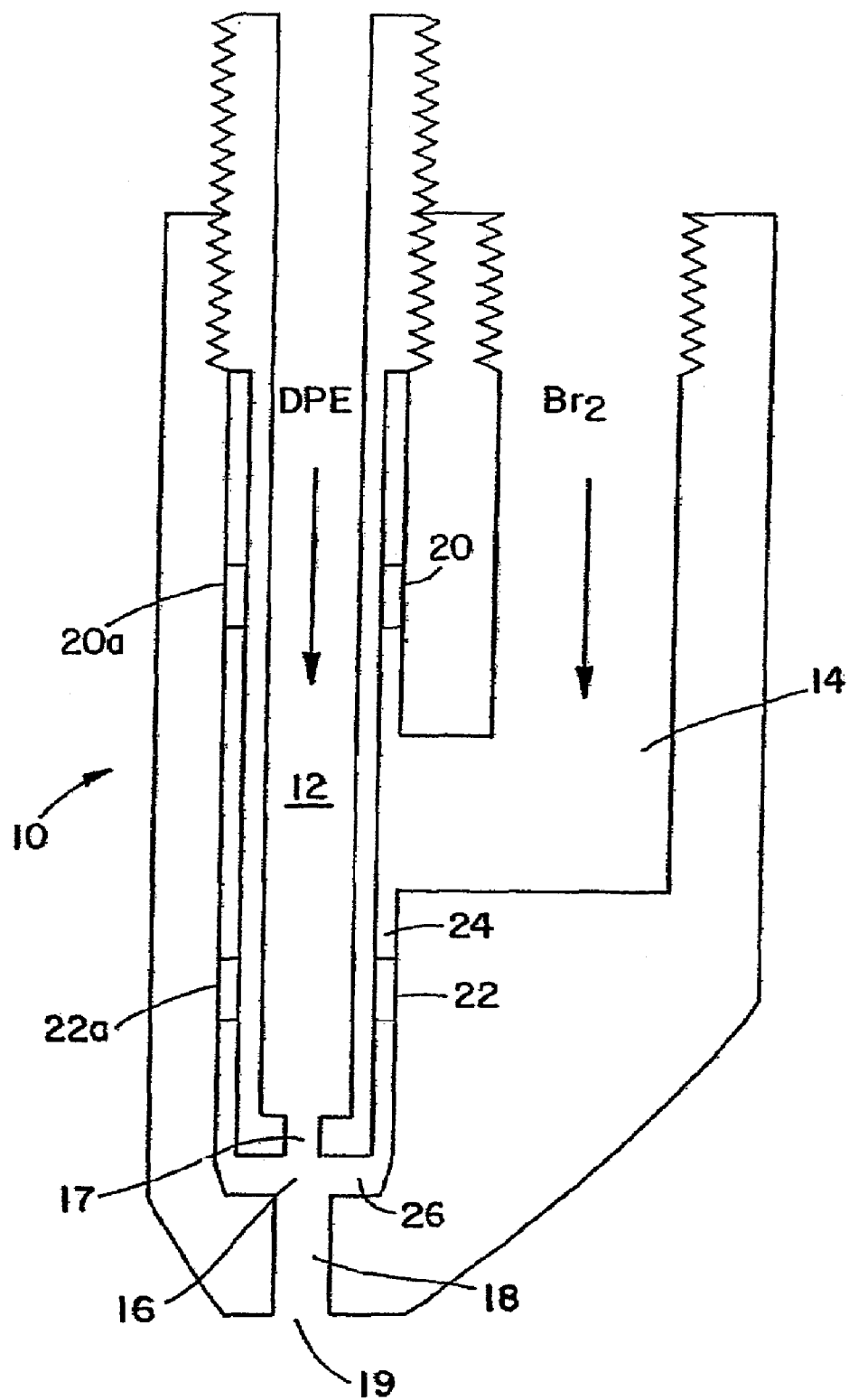
FIG. 1 is a cross-sectional, partial view of a mixer suitable for use in the practice of this invention.

The diphenylethane reactant has the formula:

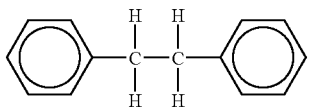

and has the IUPAC name, 1,2-diphenylethane. For convenience, this compound will be simply referred to as diphenylethane.

The diphenylethane can be produced by various routes. For example, CA 97 3865d (Japanese Kokai 82/45114) and CA 46 7084g disclose the reaction of benzene and ethylene dihalide in the presence of aluminum trichloride to yield diphenylethane.

It is not uncommon for the diphenylethane to contain impurities, especially isomeric impurities, e.g., 1,1-diphenylethane. Since such impurities can adversely affect the color of the decabromodiphenylethane product, it is desirable to reduce the impurity level. Such can be done by the use of conventional purification processes, such as recrystallization wherein the diphenylethane is dissolved in a solvent and recrystallized one or more times until the purity level sought is achieved.

The diphenylethane used in forming the bromine/diphenylethane derived mixture is preferably provided as a molten liquid due to the ease of forming an intimate mix with the bromine. To obtain the molten state, the diphenylethane is brought to a temperature which is in excess of its melting point (53° C. to 55° C./127° F. to 131° F.). Preferably, the temperature is within the range of from about 55° C. to about 80° C. (130 to 175° F.). The higher temperatures are preferred as the viscosity of the molten diphenylethane will be lower and thus facilitate the formation of the derived mixture. Most preferred is a temperature within the range of from about 70° C. to about 80° C. (160 to 175° F.).

Until it is used, it is preferred that the molten diphenylethane be blanketed by a non-oxidizing atmosphere. Such an atmosphere can be provided by most inert gases, for example, nitrogen, argon, neon, helium, krypton, xenon and the like. By providing the inert atmosphere, it has been found that the color characteristics of the final decabromodiphenylethane product are benefited. It is theorized that this color benefit is a result of preventing or at least reducing the production of oxidation decomposition impurities in the molten diphenylethane. The decomposition impurities are probably 1-hydroxy-1,2-diphenylethane, benzaldehyde, benzyl alcohols, and the like.

The bromine/diphenylethane derived mixture can also be formed by adding solid diphenylethane to the diluent bromine.

It is preferred that the bromine used in the processes of this invention be essentially anhydrous, i.e., contain less than 100 ppm water, and contain no more than 10 ppm organic impurities, e.g., oil, grease, carbonyl containing hydrocarbons, iron, and the like. With such a bromine purity, there is little, if any, impact on the color attributes of the decabromodiphenylethane product. Available, commercial grade bromine may have such a purity. If, however, such is not available, the organic impurities and water content of the bromine can be conveniently reduced by mixing together a 3 to 1 volume ratio of bromine and concentrated (94-98 percent) sulfuric acid. A two-phase mix is formed which is stirred for 10-16 hours. After stirring and settling, the sulfuric acid phase, along with the impurities and water, is separated from the bromine phase. To further enhance the purity of the bromine, the recovered bromine phase can be subjected to distillation.

The formation of the derived mixture from liquid bromine and molten diphenylethane can be accomplished by most any conventional technique for mixing two liquids. A most preferred technique is to form the mixture in a flow or line mixer to which the bromine and diphenylethane are fed. Exemplary of such mixers are, (1) jet mixers which depend upon the impingement of one stream into another stream, (2) injectors in which one liquid flow induces another liquid flow, (3) orifices and mixing nozzles in which the pressure drop is used to effect the mixing, (4) valves, and (5) pumps, especially centrifugal pumps into which the two streams are fed to the suction side. A common characteristic of these preferred mixers is that the mixing occurs quickly and thoroughly.

FIG. 1 depicts a particularly preferred jet mixer for use in the process of this invention. The jet mixer, generally designated by the numeral 10, provides a longitudinal, axially directed conduit 12 through which the liquid diphenylethane flows. Conduit 14 carries the bromine to an annular space 24 which surrounds conduit 12. Spacers 20, 20ª, 22 and 22ª locate and hold conduit 14 in position with respect to annular space 24. At the lowermost extent of annular space 24 there is radial conduit 26 which directs the bromine flow in an inward and radial direction with respect to the long axis of conduit 12. Adjacent diphenylethane discharge port 17 and radial conduit 26 is impingement chamber 16. Downstream from impingement chamber 16 is mixing chamber 18 and mixture discharge port 19.

In operation, bromine flows through conduit 14, annular space 24 and radial conduit 26 to reach impingement chamber 16. At impingement chamber 16 the bromine is traveling in an inward and radial direction. The diphenylethane flows down conduit 12 and through discharge port 17 in an axial direction with respect to impingement chamber 16. The thus flowing diphenylethane intersects and impinges perpendicularly with the flowing bromine from radial conduit 26. Subsequent to the impingement, the resulting mix flows into mixing chamber 18 and is then discharged with velocity as a stream from the mixer.

The mixer dimensions determine the velocity of the stream from the mixer and the residency time of the bromine/diphenylethane derived mix in the mixer. For any desired velocity and residency time, these dimensions can be conventionally determined. For example, on a commercial scale, for a 272 kg/hr (600 lb/hr) molten diphenylethane and a 2,400 kg/hr (5,300 lb/hr) bromine feed rate and for a mixer residency time of about 0.01 second. The height of radial conduit 26 can be 0.635 cm (¼ inch) while mixing chamber 18 can be 0.80 cm (5/16 inch) in diameter and 1.9 cm (¾ inch) long.

In those cases where the derived mixture is made from liquid bromine and solid diphenylethane, conventional liquid-solid mixing systems can be used, understanding that as the diphenylethane dissolves in the bromine it will begin to be brominated.

Subsequent to the formation of the bromine/diphenylethane derived mixture, it is preferred that the mixture be quickly fed to the reaction mass. Most preferably, the mixture is fed to the reaction mass within about 2 seconds of its formation. Generally, the time which elapses between the mixture formation and its being fed will be less than about 0.05 seconds. A preferred time is within the range of from about 0.001 to about 0.05 seconds and a most preferred range is from about 0.005 to about 0.01 seconds. The preferred and most preferred ranges are most suitable when the mixing device used to form the mixture is compromised by the evolution of the HBr gas due to the reaction of the diphenylethane and bromine.

The molar ratio of bromine to diphenylethane used to form the desired mixture lies within the range of from about 5:1 to about 30:1, and preferably within the range of from about 7.5:1 to about 25:1. Most preferably, the molar ratio lies within the range of from about 9:1 to about 25:1. Most highly preferred is a ratio within the ratio of about 10:1 to 15:1. Molar ratios in excess of 30:1 may be used; however, such excess ratios will result in more liquid bromine being present after the reaction and thus, higher attendant costs for the bromine recovery step.

The derived mixture will be comprised of bromine, and one or more of diphenylethane, mono-, di-, tri- and tetra-bromodiphenylethane. The exact composition of the derived mixture before it is fed to the reaction mass will depend upon the time that has lapsed between the formation of the mixture and its feed to the reaction mass. The more brominated species will be present in larger quantities as the time period increases since there will be sufficient time for the additional bromination to occur. In those cases where the time period is short, the derived mixture will contain more diphenylethane and/or the lower brominated species.

It is to be understood that it is permissible to have present in the derived mixture components other than bromine, diphenylethane and brominated diphenylethane provided that these components do not defeat the very reason for practicing the processes of this invention. For example, it is best that the derived mixture not contain a bromination catalyst as such catalyst can cause the above discussed-C—C-cleavage in the unprotected species. However, if the practitioner wishes to use a bromine recycle stream from a previous process run, then it is possible that the recycled bromine could contain some small concentration of a still active bromination catalyst. Considering the small amount of catalyst present, the use of such recycled bromine would be permissible as the deleterious impact of the catalyst, if any, would be so small as to be acceptable in view of the effect sought.

The bromine temperature should be sufficiently high so that when molten diphenylethane is used it is not cooled to form a solid. For most all cases, the bromine temperature is preferably within the range of from about 30° C. to about 75° C.

In commercial systems process efficiency is paramount. Thus, the feed rate of the derived mixture should be as high as is possible in view of the capacity of the reaction system to handle evolved HBr. The feed stream cross sectional area/velocity are selected so as to expend as much energy as possible in the mixing process. It has been found that smaller cross sectional areas and faster feed stream velocities will generally yield larger crystals, lower occluded bromine in the product and a better colored product. There are practical limits, however, and they are set by cost and benefit balances and available equipment, e.g., feed pumps and overhead capacity. Exemplifying suitable cross sectional areas and velocities are: the areas within the range of from about 0.03 to about 10 cm$^2$ (0.0005 to 1.6 inches$^2$) and the velocities within the range of from about 0.3 to about 30 m/sec (0.98 to 98 ft/sec). Such ranges are suitable for most stirred commercial reactors, and are especially suitable for 1000 to about 30,000 L (260 to about 8000 gal) reaction masses, all having the appropriate overhead capacities to handle and separate evolved Br$_2$ and HBr from their respective reaction masses. Preferred are cross sectional areas within the range from about 0.5 to about 2 cm$^2$ (0.08 to 0.31 inches$^2$) and velocities within the range of from about 5 to about 10 m/sec (16.4 to 32.8 ft/sec).

The derived mixture can be fed by using one or more feed streams. In those cases where there are a plurality of streams, each stream is proportioned to handle its fraction of the feed service.

The derived mixture feed stream can be introduced into the reactor either above or below the surface of the reaction mass. It is preferred that the introduction occur below the surface, say from about 2.5 cm (1 inches) to about 60 cm (24 inches) for a commercial scale reactor. If above-surface feed is used, then the point of introduction will preferably be near the surface to prevent splattering.

The reactor to which the derived mixture is fed will generally be an agitated, glass-lined reactor to which has already been charged bromine and bromination catalyst.

The charged bromination catalyst is preferably AlCl$_3$ and/or AlBr$_3$, although use may be made of aluminum powder, iron powder, FeCl$_3$ and FeBr$_3$, alone or in combination with the aluminum trihalides. Other bromination catalysts are suitable provided that they have sufficient catalytic activity to provide for the ar-perbromination needed to yield a decabromodiphenylethane product. Catalytic quantities are used. Typically, the catalysts will be present in an amount within the range of from about 0.1 to about 20 weight percent, based on the weight of the diphenylethane fed. The amount used will generally depend on the catalytic activity of the chosen catalyst, reaction temperature, and the amount of bromine used. A preferred amount is within the range of from about 2 to about 15 weight percent on the same basis. When AlCl$_3$ is the catalyst, for example, from about 5.0 to about 7.0 weight percent will be most preferred.

The bromination catalyst and bromine can be charged to the reaction vessel in any order or together. After charging, the bromine/catalyst mix will preferably be brought to a temperature within the range of about 50° C. to about 60° C. (122 to 140° F.). Lower or higher temperatures are possible, but lower temperatures may result in lower bromination while higher temperatures will require pressurized operation.

The amount of bromine in the reaction mass during the feed of the derived mixture is that amount which is sufficient to yield a stirrable reaction mass and, ultimately, a decabromodiphenylethane product (such a product is defined as a mixture of brominated diphenylethanes having an average bromine number of at least about 9.0 and preferably within the range of from about 9.5 and 10). There are two sources of bromine which will contribute bromine to the reaction mass—the bromine which accompanies the derived mixture and the bromine which is initially present in the reactor before the feed. The amount of bromine initially present in the reactor is preferably within the range of from about 25 to about 150% of the stoichiometric amount needed to produce the diphenylethane product. Most preferred is an initial bromine amount which is within the range of from about 75% to about 100% of the stoichiometric amount.

The total amount of bromine, that is the sum of the amount of initial bromine in the reactor and the amount of bromine used in forming the bromine derived mixture, will provide a molar ratio of bromine to the diphenylethane used which is within the range of from about 14:1 to about 30:1.

Preferred is a molar ratio of from about 16:1 to about 24:1 and most preferred is a molar ratio of from about 18:1 to about 20:1.

During the feed of the bromine/diphenylethane derived mixture, the reaction mass temperature is kept within the range of from about 30° C. to about 80° C., and preferably within the range of from about 50° C. to about 60° C. Since the bromination of diphenylethane is exothermic, cooling of the reaction mass is needed to maintain the reaction mass temperature chosen. The heat of reaction can be removed from the reaction mass by cooling the reaction vessel or by having the reaction mass under reflux conditions so that heat can be removed by the use of an overhead condenser.

It is preferred that the pressure in the reaction vessel be that which provides a refluxing condition at the selected reaction mass temperature. With a refluxing condition, control of the reaction mass temperature is facilitated. If temperature control is effected otherwise, i.e., by the use of heating or cooling jackets, then the pressure can be any which is not prohibitive of the obtainment of the various defined parameters of the process. Also, since temperatures above the boiling point of bromine are useful in the process of this invention, super atmospheric pressures, e.g., 15 psig can be used to obtain same.

The process of this invention is benefited by the fact that, after the feed of the derived mixture feed to the reactor is completed, no further lengthy maintenance of the formed reaction mass is needed to complete the bromination reaction to obtain the decabromodiphenylethane product. The bromination reaction after the feed has been completed is best monitored by detecting HBr evolution from the reaction mass. Cessation of HBr evolution signals the end of the bromination reaction. With the process of this invention the bromination reaction is usually finished within one minute of the cessation of the derived mixture feed. Thus, product recovery can occur quite soon after the derived mixture feed is completed. It is to be understood that the practitioner can wait for some time to recover the product as no harm is done except that process cycle time is extended.

After the bromination reaction has at least substantially ceased, the reaction mass will comprise a liquid solid mixture. The solid comprises a precipitate which includes decabromodiphenylethane product, occluded free bromine and other impurities. The liquid will comprise mostly bromine and catalyst. Before recovering the solid, it is preferred to first deactivate the catalyst. Deactivation can be accomplished by introducing water to the reaction mass or vice versa. Generally, it is preferred to move the reaction mass from the reactor to a stripping vessel. The stripping vessel will contain water which (1) deactivates the catalyst and (2) which will provide for the formation of a slurry after the bromine is stripped off.

Once in the stripping vessel, the reaction mass, which comprises the solids and the bromine, forms one phase and the water, the other phase. The water phase is on top. The vessels contents are heated to boil-off or strip the bromine. The stripping temperature is generally around 57° C. (135° F.). The bromine boils off and passes through the water phase and takes a small amount of water with it. As more bromine is stripped, the solids and bromine phase begins to thicken. At the point where there is approximately an equal weight of bromine and solids, the solids will begin to transit into the water phase. As more bromine is stripped, the remaining solids will slurry with the water. The solids, principally decabromodiphenylethane product, do not wet well in water. The larger decabromodiphenylethane product particles tend to settle in the water. The fines, and there are always some, do not, for the most part, settle, but instead move to the top of the water surface and form a froth. The more fines, the worse the froth formation and the slower the stripping must proceed. Since the practice of the process of this invention results in an abatement of the fines production, there is an attendant reduction in froth production. Thus, it is possible, with the practice of this invention, to use a higher stripping rate. Increases in stripping rates of up to 100% have been experienced by the practice of this invention.

After the bromine has been stripped off, the water and solids slurry is treated with an aqueous base to neutralize any HBr present. The aqueous base can be any suitable base, e.g., an aqueous solution of NaOH or $Na_2CO_3$.

After the neutralization step, the slurry in the stripper vessel is removed therefrom and is processed to separate the liquid portion from the solids portion. This is most easily accomplished by centrifuging. It is at this centrifuging step that another process benefit is realized due to the reduction of fines production. When a large quantity of fines are present, the centrifuging time is substantially lengthened as the fines interfere with the separating movement of water from the solids portion of the slurry. By having a low fines production, there has been seen a 50-60% reduction in centrifugation times.

The undried solids recovered from the slurry are referred to herein by the term "wet cake". This term is not meant to be restricted by any particular manner of solids recovery and/or by ancillary treatments of the slurry or recovered solids, e.g., neutralization, washing and the like. Most often the wet cake is recovered from the filter media as a cake-like material.

The wet cakes obtained in accordance with this invention are unique in that they have a relatively low occluded free bromine content, say from about 500 ppm to about 2000 ppm and most probably from about 900 ppm to about 1200 ppm. Compare wet cakes having a high, e.g., 3500 ppm, occluded free bromine content and which are produced by processes which do not use highly diluted diphenylethane feeds. These wet cakes have a high, e.g., 3500 ppm, occluded free bromine content.

The term "occluded free bromine" refers to that bromine which is tightly held by the recovered decabromodiphenylethane product component of the wet cake so that ordinary washing techniques are insufficient to reduce its content in the product.

The wet cake is preferably submitted to a dry and grind technique, such as that provided by a hammer mill, e.g., Raymond Mill. The combination of drying and grinding yields a dry powder of reduced average particle size and reduced occluded free bromine content. Preferred drying temperatures are within the range of from about 150 to about 350° C. (302 to 662° F.). The grinding is preferably designed to reduce the average particle size of the decabromodiphenylethane product to be within a range of from about 3 to about 5 microns. Both of the above dry and grind conditions can be obtained by the use of a hammer mill. In some instances, it may be preferred that the heating occur prior to the grinding step; however, the reverse order is usable and functional. After the grind and dry step the resultant dry decabromodiphenylethane product will still contain some occluded free bromine. In these cases, and that will be the case in most situations, the product will still contain 700 to 1000 ppm occluded free bromine. This level still exceeds the more acceptable and desired occluded free bromine level of 150 to 200 ppm occluded free bromine.

The color of a wet cakes also evidences its occluded free bromine content. Compare a Yellowness Index (YI), as measured by ASTM D-1925, of about 24 for the dried and ground wet cakes produced with undiluted molten diphenylethane against a YI of from about 12 to about 18 for dried and ground wet cakes of this invention.

To further reduce the occluded free bromine content of the ground and dried product so as to obtain the acceptable level, the product is oven-aged at a temperature within the range of from about 175° C. to about 290° C. (350° F. to about 550° F.) for about 1 to about 20 hours. The higher temperatures use the shorter heating times while the lower temperatures need the longer heating times. A preferred temperature range is from about 230 to about 260° C. (446 to 500° F.). With these preferred temperatures, the oven-aging time is from about 3 to about 9 hours. A comparison against decabromodiphenylethane processes which use undiluted molten diphenylethane feeds, shows that such processes need longer aging times, 6 to 20 hours, at comparable temperatures, to obtain the same level of occluded free bromine in the final product.

The oven-aging produces the final decabromodiphenylethane product which will, preferably, be principally comprised of at least about 90 wt % (and more preferably from about 95 wt % to about 99.8 wt %) of decabromodiphenylethane and smaller amounts of nonabromodiphenylethane, octabromodiphenylethane, and decabromostilbene with an occluded free bromine content within the range of from about 100 ppm to about 300 ppm.

The decabromodiphenylethane product of this invention may be used as a flame retardant in formulation with virtually any flammable material. The material may be macromolecular, for example, a cellulosic material or a polymer. Illustrative polymers are: olefin polymers, cross-linked and otherwise, for example, homopolymers of ethylene, propylene, and butylene; copolymers of two or more of such alkylene monomers and copolymers of one or more of such alkylene monomers and any other copolymerizable monomers, for example, ethylene/propylene copolymers, ethylene/ethyl acrylate copolymers and ethylene/vinyl acetate copolymers; polymers of olefinically unsaturated monomers, for example, polystyrene, e.g., high impact polystyrene, and styrene copolymers; polyurethanes; polyamides; polyimides; polycarbonates; polyethers; acrylic resins; polyesters, especially poly(ethyleneterephthalate) and poly(butyleneterephthalate); epoxy resins; alkyds; phenolics; elastomers, for example, butadiene/styrene copolymers and butadiene/acrylonitrile copolymers; terpolymers of acrylonitrile, butadiene and styrene; natural rubber; butyl rubber; and polysiloxanes. The polymer may also be a blend of various polymers. Further, the polymer may be, where appropriate, cross-linked by chemical means or by irradiation.

The amount of decabromodiphenylethane product used in a formulation will be that quantity needed to obtain the flame retardancy sought. It will be apparent to the practitioner that for all cases no single precise value for the proportion of the product in the formulation can be given since this proportion will vary with the particular flammable material, the presence of other additives and the degree of flame retardancy sought in any given application. Further, the proportion necessary to achieve a given flame retardancy in a particular formulation will depend upon the shape of the article into which the formulation is to be made, for example, electrical insulation, tubing and film will each behave differently. In general, however, the formulation may contain from 5 to 40 weight percent, preferably 10 to 30 weight percent, of the product when it is the only flame retardant compound in the formulation.

It is especially advantageous to use the flame retardant final product of this invention with an inorganic compound, especially ferric oxide, zinc oxide, zinc borate, the oxide of a Group V element, for example, bismuth, arsenic, phosphorus and especially antimony, in the formulation. Of these compounds, antimony oxide is especially preferred. If such a compound is present in the formulation, the quantity of product needed to achieve a given flame-retardancy is accordingly reduced. Generally, the product and the inorganic compound are in a weight ratio of from 1:1 to 7:1, and preferably of from 2:1 to 4:1.

Formulations containing a flame retardant system comprised of the product of this invention and the above inorganic compounds may contain up to about 40 percent by weight of the system and preferably between 20 percent and 30 percent by weight.

Any of the additives usually present in formulations, e.g., plasticizers, antioxidants, fillers, pigments, and UV stabilizers can be used in formulation with the product of this invention.

Thermoplastic articles formed from formulations containing a thermoplastic polymer and a product of this invention can be produced conventionally, e.g., by injection molding, extrusion molding, compression molding, and the like.

The following Examples merely illustrate the invention described herein and are not to be taken as limiting such inventions.

EXAMPLE I

To a 15,140 L (4,000 gal) glass lined agitated reactor is added 12,712 kg (28,000 lb) of bromine. The agitator was then started and 68 kg (150 lb) $AlCl_3$ was added. The reaction content was heated to 58° C. (135° F.).

Bromine flow through a mixer was established at 2,406 kg/hr (5300 lb/hr). A bromine heater was used to obtain a temperature for the bromine of between 50° C. and 55° C. (120° F. and 130° F.). Molten diphenylethane flow to the mixer was then established at 272 kg/hr (600 lb/hr).

The mixer was located at the end of a dip tube which extended to a point 60 cm (24 inches) beneath the reaction mass surface. The mixer was of the type shown in FIG. 1 hereof. The mixer was designed to handle 272 kg/hr (600 lb/hr) diphenylethane and 2406 kg/hr (5300 lb/hr) bromine. The mixer forced the bromine radially inward into a 0.48 cm (3/16 inch) stream of diphenylethane. The mixer provides a mixing chamber through which the resultant intimate mix then passes. The chamber had a 0.8 cm (5/16 inch) diameter and was 1.9 cm (3/4 inch) long. The stream leaving the mixer had a diameter of about 0.8 cm (5/16 inch) and a velocity of about 6.1 m/sec (20 ft/sec).

The reaction mass temperature rose to reflux temperature, which was about 60° C. (140° F.), at a reaction pressure of 2.05×105 PA (15 psig).

The diphenylethane and bromine were allowed to flow until 1090 kg (2400 lb) of diphenylethane had been fed. Subsequently, the diphenylethane flow was stopped and nitrogen was blown through the diphenylethane passages. The bromine flow was stopped and nitrogen was blown through its passages.

The reaction mass was transferred to a stripping vessel to which had been previously added 6000 L (1500 gal) of water. The resulting mix was then heated and stirred to a temperature of about 58° C. (135° F.) so as to obtain the boil-off of the bromine. A 1% aqueous solution of Aerosol™-OTB made by American Cyanamide was used as a wetting agent. The boil-off period lasted about 4 hours.

After the boil-off, the remaining solids and water slurry was treated with a base to neutralize and acidic components. The neutralized slurry was fed over a 2.5 hour period to a centrifuge to yield a wet cake. The wet cake was then recovered and fed to a Raymond Mill wherein the wet cake was dried and ground. The wet cake was dried at a temperature of 205° C. (400° F.) for a period of 2 seconds and ground to an average particle size of from about 80 to about 4.5 microns.

The foregoing procedure was repeated several times except that in three of the runs, 23-26 minutes was used to get the bromine flow and temperature established. In another run, 4 minutes was used.

Comparative runs were made in which the diphenylethane was fed to the reactor alone.

Comparative Runs

To a 15,140 L (4,000 gal) glass lined agitated reactor was added 21,760 kg (48,000 lb) of bromine. The agitator was then started and 68 kg (150 lb) $AlCl_3$ was added. The reactor contents were heated to 58° C. (135° F.).

Molten diphenylethane flow to a dip tube was then established at 272 kg/hr (600 lb/hr). The dip tube extended to a point 120 cm (48 inches) beneath the reaction mass surface.

The diphenylethane was allowed to flow until 1089 kg (2400 lb) diphenylethane had been fed. Subsequently, the diphenylethane flow was stopped and nitrogen was blown through the diphenylethane dip tube.

The reaction mass was transferred to a stripping vessel to which had been previously added 6000 L (1500 gal) of water. The resulting mix was then heated and stirred to a temperature of about 58° C. (135° F.) so as to obtain the boil-off of the bromine. A 1% aqueous solution of Aerosol™-OTB made by American Cyanamide was used as a wetting agent. The boil-off period lasted about 8 hours.

After the boil-off, the remaining solids and water slurry was treated with a base to neutralize and acidic components. The neutralized slurry was fed over a 5 hour period to a centrifuge to yield a wet cake. The wet cake was then recovered and fed to a Raymond Mill wherein the wet cake was dried and ground. The wet cake was dried at a temperature of 205° C. (400° F.) for a period of 2 seconds and ground to an average particle size of from about 80 to about 4.5 microns.

Measurements were obtained from all of the runs for (1) the bromine boil-off rate, (2) the centrifugation rate, (3) the occluded free-bromine content of the wet cake before and after Raymond Milling, and (4) the color values of the Raymond Milled product.

Using the process of this invention resulted in an average 75% increase in the boil-off rate and an average 97% increase in the centrifugation rate. The wet cake from the comparative runs had, on average, 78% (8 samples, 2,007 to 5,463 ppm, avg. 3,773 ppm occluded $Br_2$) more occluded free bromine than did the wet cakes produced by the process of this invention (8 samples, 1,308 to 838 ppm, avg. 1,122 ppm occluded $Br_2$). After Raymond Milling, the occluded free bromine content of the comparatively dried and ground products was, on average, 225% higher than for the dried and ground products of this invention. Compare, for the comparative 8 samples, 1,331 to 4,771 ppm, avg. 3,117 ppm occluded $Br_2$ and for the dried and ground products of this invention, 8 samples, 499 to 1232 ppm, avg. 890 ppm occluded $Br_2$. Based upon the Yellowness Index (YI), the Raymond Milled products of this invention have a better color than the comparative products. The YI values, ASTM D-1925, for the dried and milled material produced in accordance with this invention, prior to oven-aging, lie within the range of from about 12.5 to about 17.5 whereas the comparative samples have a YI between about 22 to about 26.

That which is claimed is:

1. A process for bromination of diphenylethane, which process comprises:
    a) forming a mixture of at least bromine and molten diphenylethane; and
    b) feeding said mixture into a stirrable reaction mass comprising bromine and a bromination catalyst to form a decabromodiphenylethane product;
wherein said catalyst is present in an amount within the range of from about 0.1 to about 20 weight percent, based on the weight of said diphenylethane, and wherein at least a portion of the bromine in a) is from a bromine recycle stream.

2. A process as in claim 1 wherein said amount of catalyst is within the range of from about 2 to about 15 weight percent based on the weight of said diphenylethane.

3. A process as in claim 1 wherein said catalyst used is selected from $AlCl_3$, $AlBr_3$ and a mixture thereof.

4. A process as in claim 1 wherein said catalyst is $AlCl_3$, $AlBr_3$ or a mixture thereof in combination with aluminum powder, iron powder, $FeCl_3$ or $FeBr_3$.

5. A process as in claim 1 wherein said mixture is fed below the surface of said reaction mass.

6. A process for the manufacture of a decabromodiphenylethane product, which process comprises:
    a) generating a mixture from at least bromine and molten diphenylethane in a molar ratio of bromine to molten diphenylethane of at least about 5:1; and
    b) feeding said mixture into a stirrable reaction mass comprising bromine and a bromination catalyst,
    wherein at least a portion of the bromine in a) is from a bromine recycle stream.

7. A process as in claim 6 wherein said molar ratio is within the range of from about 5:1 to about 30:1.

8. A process as in claim 7 wherein the molar ratio is within the range of from about 7.5:1 to about 25:1.

9. A process as in claim 7 wherein the reaction mass temperature is within the range of from about 30 to about 80° C.

10. A process as in claim 7 wherein the mixture is fed to the reaction mass within about 2 seconds after the mixture is formed.

11. A process as in claim 10 wherein there is a catalytic amount of bromination catalyst present in the reaction mass and such catalyst is selected from $AlCl_3$, $AlBr_3$ and a mixture thereof.

12. A process as in claim 10 wherein there is an initial amount of bromine in the reaction mass before the mixture feed begins, which initial amount is within the range of from about 25 to about 150% of the stoichiometric amount needed to produce a decabromodiphenylethane product from the diphenylethane fed.

13. A process as in claim 7 wherein there is a catalytic amount of bromination catalyst present in the reaction mass and such catalyst is selected from $AlCl_3$, $AlBr_3$ and a mixture thereof.

14. A process as in claim 7 wherein there is an initial amount of bromine in the reaction mass before the mixture feed begins, which initial amount of bromine is within the range of from about 25 to about 150% of the stoichiometric amount needed to produce a decabromodiphenylethane product from the diphenylethane to be fed.

15. A process as in claim 6 wherein the molar ratio is within the range of from about 10:1 to about 15:1; the mixture is fed to the reaction mass within about 0.001 to about 0.05 second of its being formed; there is a catalytic amount of a bromination catalyst present in the reaction mass and such catalyst is selected from $AlCl_3$, $AlBr_3$ and a mixture thereof; and there is an initial amount of bromine in the reaction mass before the mixture feed begins, which initial amount of bromine is within the range of from about 75 to about 100% of the stoichiometric amount needed to produce a decabromodiphenylethane product from the diphenylethane to be fed.

16. A process as in claim 7 wherein the mixture is fed to the reaction mass within about 2 seconds of its being formed, wherein there is a catalytic amount of bromination catalyst present in the reaction mass and such catalyst is selected from $AlCl_3$, $AlBr_3$ and a mixture thereof, wherein there is an initial amount of bromine in the reaction mass before the mixture feed begins, which initial amount of bromine is within the range of from about 25 to about 150% of the stoichiometric amount needed to produce a decabromodiphenylethane product from the diphenylethane to be fed, wherein in a) the molten diphenylethane is at a temperature in the range of from about 55° C. to about 80° C., wherein the molten diphenylethane is blanketed by a non-oxidizing atmosphere at least until it is fed into said reaction mass, and wherein the bromine in a) is at a temperature within the range of from about 30° C. to about 75° C.

17. A process as in claim 7 wherein in a) the molten diphenylethane is at a temperature in the range of from about 55° C. to about 80° C.

18. A process as in claim 7 wherein the bromine in a) is at a temperature within the range of from about 30° C. to about 75° C.

19. A process as in claim 6 wherein the molten diphenylethane is blanketed by a non-oxidizing atmosphere at least until it is fed into said reaction mass.

20. A process as in claim 6 wherein said process is conducted with a reaction mass volume larger than about 1000 liters.

* * * * *